(12) United States Patent
Malik

(10) Patent No.: US 8,834,174 B2
(45) Date of Patent: Sep. 16, 2014

(54) METHODS AND SYSTEMS FOR ASSESSING LATENT TRAITS USING PROBABILISTIC SCORING

(75) Inventor: Alan David Malik, Littleton, CO (US)

(73) Assignee: Patient Tools, Inc., Littleton, CO (US)

( * ) Notice: Subject to any disclaimer, the term of this patent is extended or adjusted under 35 U.S.C. 154(b) by 38 days.

(21) Appl. No.: 13/405,089

(22) Filed: Feb. 24, 2012

(65) Prior Publication Data

US 2012/0270199 A1 Oct. 25, 2012

Related U.S. Application Data

(60) Provisional application No. 61/446,220, filed on Feb. 24, 2011.

(51) Int. Cl.
*G09B 7/00* (2006.01)
*A61B 5/16* (2006.01)
*A61B 5/00* (2006.01)
*G06F 19/00* (2011.01)

(52) U.S. Cl.
CPC ............... *A61B 5/16* (2013.01); *A61B 5/7475* (2013.01); *G06F 19/345* (2013.01); *A61B 5/0002* (2013.01); *G06F 19/363* (2013.01)
USPC .......................................... 434/322; 434/236

(58) Field of Classification Search
USPC ................. 434/322, 323, 350–353, 365
See application file for complete search history.

(56) References Cited

U.S. PATENT DOCUMENTS

| 5,059,127 A | 10/1991 | Lewis et al. |
| 5,435,324 A * | 7/1995 | Brill ......................... 128/897 |
| 5,572,421 A | 11/1996 | Altman et al. |
| 5,868,669 A | 2/1999 | Iliff |

(Continued)

FOREIGN PATENT DOCUMENTS

| EP | 0789307 A1 | 8/1997 |
| WO | 2004/080312 A1 | 9/2004 |
| WO | 2010/045463 A2 | 4/2010 |

OTHER PUBLICATIONS

Jonathan Shedler, PhD. et al., "Practical Mental Health Assessment in Primary Care", The Journal of Family Practice, Jul. 2000, vol. 49, No. 7, 8 pages.

(Continued)

*Primary Examiner* — Robert J Utama
*Assistant Examiner* — Sadaruz Zaman
(74) *Attorney, Agent, or Firm* — Marsh Fischmann & Breyfogle LLP

(57) ABSTRACT

A method and system for assessing a latent trait such as a psychiatric disorder in a test subject. The method includes receiving a test subject's responses to test items that are administered to the test subject to elicit the responses from the test subject. An initial first sub-region probability of the test subject lying within a first sub-region of a first latent trait is determined from the test subject's response to the initial first test item. A subsequent first sub-region probability of the test subject lying within the first sub-region of the first latent trait is then determined using the test subject's response to the subsequent first test item to ascertain a conditional response probability, and using the initial first sub-region probability as a prior first sub-region probability. The method and system can be used to more accurately and/or more rapidly assess one or more latent traits in a test subject.

37 Claims, 13 Drawing Sheets

(56) References Cited

U.S. PATENT DOCUMENTS

| | | | |
|---|---|---|---|
| 6,053,866 | A | 4/2000 | McLeod |
| 6,108,665 | A | 8/2000 | Bair et al. |
| 6,322,503 | B1 * | 11/2001 | Sparhawk, Jr. ............... 600/300 |
| 6,655,963 | B1 * | 12/2003 | Horvitz et al. ................ 434/236 |
| 6,687,685 | B1 * | 2/2004 | Sadeghi et al. ................ 706/15 |
| 7,590,609 | B2 | 9/2009 | Verlinden et al. |
| 7,783,582 | B2 * | 8/2010 | Doctor et al. .................. 706/12 |
| 2002/0035486 | A1 | 3/2002 | Huyn et al. |
| 2005/0197988 | A1 | 9/2005 | Bublitz |
| 2005/0222799 | A1 * | 10/2005 | Bolt et al. .................... 702/127 |
| 2009/0004638 | A1 * | 1/2009 | Stout et al. ................... 434/353 |
| 2009/0281398 | A1 | 11/2009 | Hogan |
| 2013/0122474 | A1 * | 5/2013 | Thomas ........................ 434/236 |

OTHER PUBLICATIONS

Ronald K. Hambleton et al., "Comparison of Classical Test Theory and Item Response Theory and Their Applications to Test Development", An NCME Instructional Module on Educational Measurement: Issues and Practice, pp. 253-262, (1993).

David J. Spiegelhalter et al., "An Introduction to Bayesian Methods in Health Technology Assessment", Department of Epidemiology and Public Health, University of Leicester, Aug. 21, 1999, pp. 508-512.

Invitation to Pay Additional Fees (Form PCT/ISA/206) peratining to International Application No. PCT/US2012/026629 (mailed Feb. 5, 2014).

International Search Report and Written Opinion of the International Searching Authority dated Apr. 25, 2014, PCT Application No. PCT/US2012/026629, filed Feb. 24, 2012, 17 pages.

International Preliminary Report on Patentability and Written Opinion of the Interantional Searching Authority dated May 22, 2014, PCT Application No. PCT/US2012/026629, filed Feb. 24, 2012, 10 pages.

* cited by examiner

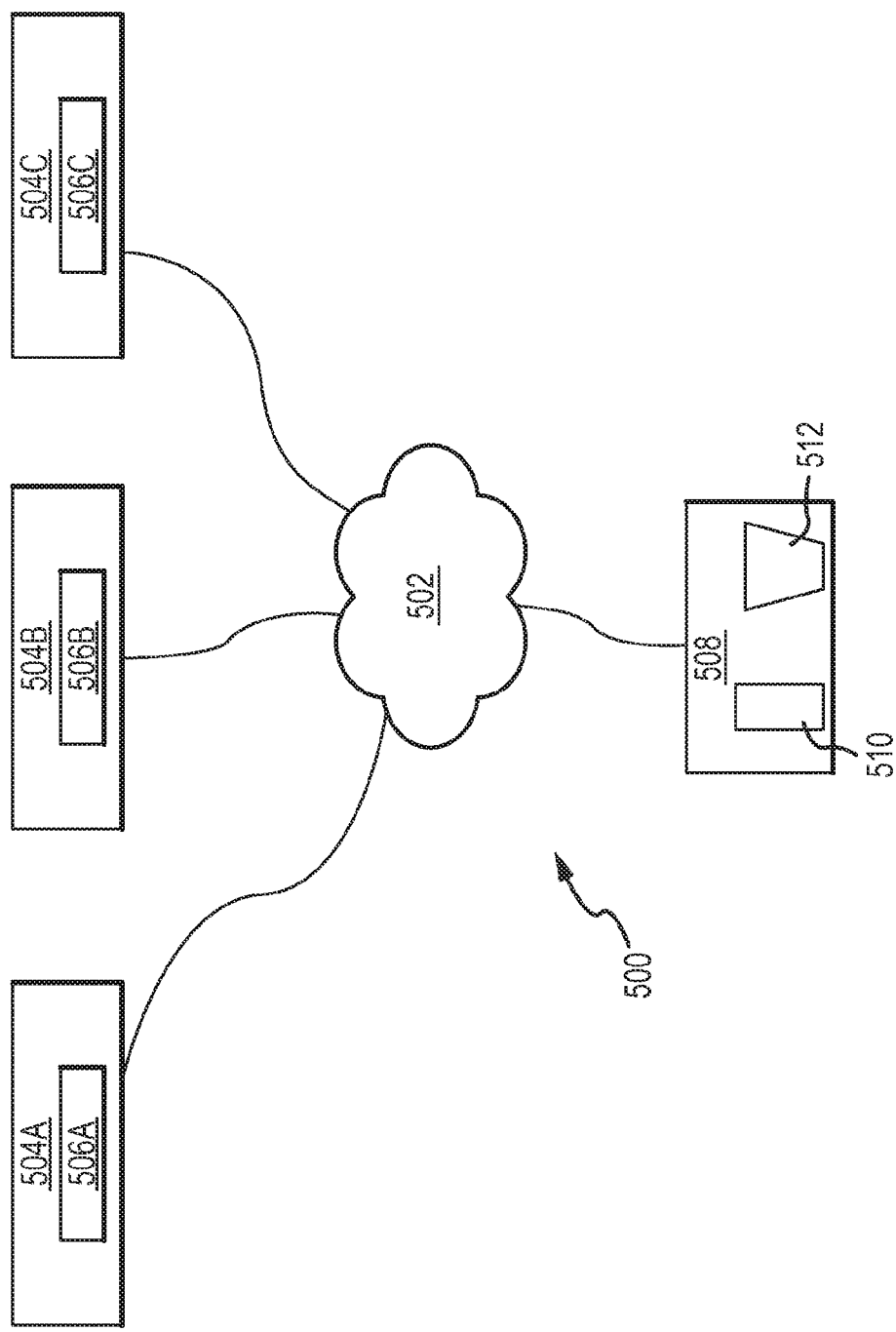

METHODS AND SYSTEMS FOR ASSESSING LATENT TRAITS USING PROBABILISTIC SCORING

RELATED APPLICATION

This application claims priority to U.S. Provisional Patent Application No. 61/446,220, filed Feb. 24, 2011, and entitled "METHODS AND SYSTEMS FOR ASSESSING LATENT TRAITS USING PROBABILISTIC SCORING", the entirety of which is hereby incorporated by reference.

BACKGROUND OF THE INVENTION

1. Field of the Invention

This invention relates to the field of psychometrics, the branch of psychology relating to the design, administration, and interpretation of test instruments (e.g., questionnaires) for assessing psychological variables (e.g., latent traits). Specifically, the invention relates to the dynamic application of probability models (e.g., probabilistic scoring) to responses to test items (e.g., questions) as a basis for assessing latent traits in a test subject.

2. Description of Related Art

Psychometrics relates to the theory and technique of psychological measurement, which can include the measurement of latent traits such as intelligence, abilities, attitudes, personality traits or psychiatric disorders. Psychometrics is primarily concerned with the construction and validation of measurement instruments, such as questionnaires and other types of tests that elicit responses from a test subject, upon which the measurement of the latent trait is based.

In psychometrics, item response theory (IRT) is a paradigm for the design, analysis and scoring of psychometric measurement instruments. The term "item" is used because while many test items may be questions that have incorrect and correct responses (e.g., multiple choice questions), test items may also include statements that allow test subjects to indicate a level of agreement or disagreement (e.g., on a Likert scale), or to indicate symptoms that are scored as present or absent. IRT is based on the concept that the probability of a particular response to a test item is a function of person parameters and test item parameters. The person parameter may be a latent trait; it may, for example, represent a person's intelligence, the strength of an attitude, or the presence and/or severity of a psychiatric disorder. Test item parameters can include, e.g., item difficulty and item discrimination.

IRT models the relationship between latent traits and responses to test items. Among other advantages, IRT can provide a basis for obtaining an estimate of the location of a test subject on a given latent trait (e.g., the severity of a psychiatric disorder), as well as the standard error of measurement of that location. A common way to represent a location of a test subject on a given latent trait is by computing an estimated severity score, which is useful for measuring change in the test subject over time (e.g., during treatment), and/or for categorizing the test-subject into sub-regions of the latent trait.

For example, a common psychometric test instrument used to measure depression in test subjects is the PHQ-9 self-report assessment questionnaire, which computes a severity score ranging from zero for "no depression" to 27 for "extreme depression". Alternatively, the PHQ-9 can categorize depression into sub-regions of "Not Clinically Depressed" (a severity score of 0-6), "Sub-Threshold Depression" (a severity score of 7-9), or "Major Depression" (a severity score of 10 or more). See FIG. 1.

Validation of the results from a depression test instrument like the PHQ-9 would normally use a trained professional (e.g., a psychologist or psychiatrist) to independently assess a criterion measure of depression as an estimate of "ground truth" about depression in the test subject. If the criterion measure is collected at the time of the test instrument assessment then the validation is concurrent. If the criterion measure is collected at a later time then the validation is predictive. How accurately the instrument's computed result (e.g., major depression) matches the ground truth criterion is statistically expressed as the instrument's sensitivity and specificity.

An instrument's sensitivity is the percentage of time that when the criterion measure (e.g., a psychologist's assessment) finds the test subject located in a sub-region, the measurement instrument also finds the test subject located in that same sub-region. Stated another way, sensitivity can be used to express the likelihood of the occurrence of a "false-negative" where the condition goes undetected by the test instrument. For example, the PHQ-9 sensitivity for Major Depression is estimated to be 88%, meaning that on average out of 100 times that a psychologist would find a patient to have major depression, the PHQ-9 would detect 88 of those cases. The remaining 12 cases (false-negatives) would go undetected by the PHQ-9.

Conversely, a test instrument's specificity is the percentage of time that when the criterion measure finds the test subject is not located in a sub-region, the measurement instrument also finds the test subject is not located in that same sub-region. Stated another way, the specificity can be used to express the likelihood of the occurrence of a "false-positive" where the condition is misdiagnosed by the measurement instrument. For example, the PHQ-9 specificity for Major Depression is also estimated to be 88%, meaning that on average out of 100 times when a psychologist would find a patient to not have Major Depression, the PHQ-9 would agree for 88 of those cases. The remaining 12 cases (false-positives) would be detected as having Major Depression by the PHQ-9 even though a psychologist would not agree.

Many patients experiencing symptoms that might be associated with a psychiatric disorder initially seek treatment from a primary care physician. The PHQ-9 is commonly used to screen patients for depression in a primary care setting and the false-positive and false-negative findings can significantly impact the costs associated with patient care. For example, assume that a primary care physician screens 120 patients a week of which 18 patients (15%) have Major Depression and the remaining 102 patients do not have Major Depression. Screening with the PHQ-9 which has 88% sensitivity and 88% specificity, about 2 of the patients with Major Depression will go undetected (e.g., a false-negative) and about 12 of the patients without Major Depression will be detected as having Major Depression (e.g., a false-positive). The 12 false-positive patients will require additional and unnecessary diagnosis and treatment, while the 2 false-negative patients will go untreated, consuming additional medical resources especially when there are co-morbid chronic conditions, such as diabetes or cardiac risk. As another example, the Quick PsychoDiagnostic (QPD) Panel, another self-report measurement instrument, has 81% sensitivity and 96% specificity for Major Depression, and in the foregoing scenario would result in about 3 to 4 patients with Major Depression going undetected and about 4 patients without Major Depression being falsely diagnosed. Measurement accuracy has a significant impact on cost.

In addition to concerns with measurement accuracy, primary care physicians find many instruments too cumbersome and time consuming for routine use. The instruments take a significant amount of time to administer and score, and can therefore disrupt office routines and patient flow. These problems also arise when such instruments are used in an emergency room setting, e.g., for triage. Further, many instruments provide only numeric scores, not specific assessments that can better inform treatment decisions. Also, many such instruments test for one latent trait only (e.g., depression) and do not test for other psychiatric disorders that often coexist with depression and have implications for treatment of the patient.

SUMMARY OF THE INVENTION

There is a need for improved accuracy (e.g., increased sensitivity and/or increased specificity) when measuring latent traits in a test subject using a psychometric measurement instrument. There is also a need for decreasing the average time required by a test subject to complete a psychometric measurement instrument such as a questionnaire, particularly when implementing a test for multiple latent traits such as depression, generalized anxiety disorder, post traumatic stress disorder (PTSD) and the like. There is also a need for a psychometric measurement instrument that has a high sensitivity to change, particularly at the transitions between adjacent sub-regions of a latent trait.

In one embodiment, a method for assessing a latent trait in a test subject is provided. The method includes the step of receiving a test subject's responses to at least an initial first test item and to a subsequent first test item. For example, a graphical user interface (GUI) may be provided for allowing the input of the test subject's first test item responses to a plurality of first test items that are administered to the test subject to elicit the first test item responses from the test subject. The method also includes the step of determining an initial first sub-region probability of the test subject lying within a first sub-region of a first latent trait from the test subject's response to the initial first test item. The method also includes the step of determining a subsequent first sub-region probability of the test subject lying within the first sub-region of the first latent trait using: (i) the test subject's response to the subsequent first test item to ascertain a conditional response probability; and (ii) the initial first sub-region probability as a prior first sub-region probability. The determining step may be carried out, for example, using one or more processors (e.g., microprocessor).

In one aspect, the conditional response probability is ascertained from one or more validated evidence data sets. In another aspect, the method further includes the step of determining a further first sub-region probability of the test subject lying within the first sub-region of the first latent trait, using: (i) the test subject's response to a further test item to ascertain a further conditional response probability; and (ii) the subsequent first sub-region probability as a prior sub-region probability.

In another aspect, the method further includes the step of determining an initial second sub-region probability of the test subject lying in a second sub-region of the first latent trait from the test subject's first test item response to the initial first test item and determining a subsequent second sub-region probability of the test subject lying within the second sub-region of the first latent trait. According to this aspect, the method may also include the step of determining a differential probability value between the probability of the first and second sub-regions of the first latent trait, after determining the subsequent sub-region probability of the test subject lying within the second sub-region and determining a subsequent sub-region probability of the test subject lying within the first sub-region. Such a method may further include the step of administering the plurality of first test items to the test subject through a GUI. For example, the first test items may be administered to the test subject sequentially. As such, the method may include the step of terminating the administering of the first test items to the test subject when the differential probability value reaches a terminus differential probability value that meets or exceeds a threshold differential probability value. Further, a severity score may be determined for the first latent trait in the test subject from the differential probability value. The severity score may be determined, for example, by mapping the differential probability value to a severity score validated evidence data set.

The first latent trait may be, for example, a psychiatric disorder, such as depression or the like.

In another aspect, the subsequent sub-region probabilities of all first latent trait sub-regions may be determined and normalized to one. In another aspect, the plurality of first test items may include agreement test items that elicit the test subject to indicate a level of agreement of disagreement with a concept. For example, the agreement test items may elicit a level of agreement on a Likert scale. Test items may also include physiological test items that elicit the test subject to indicate the presence or absence of a physiological condition.

In another aspect, the initial first sub-region probability may be determined using an apriori probability of the test subject lying in the first sub-region of the first latent trait. In another aspect, the initial and subsequent first sub-region probabilities may be determined using Bayesian inferences. In another aspect, the step of administering the plurality of first test items to the test subject may include administering at least three first test items to the test subject, such as at least four first test items.

In another aspect, the method may further include the steps of receiving the test subject's responses to a plurality of second test items that are administered to the test subject to elicit second test item responses from the test subject. Thereafter, an initial first sub-region probability of the test subject lying within a first sub-region of a second latent trait may be determined from: (i) the test subject's response to an initial test item from the plurality of second test items to ascertain a conditional sub-region probability for the second latent trait; and (ii) the subsequent first sub-region probability of the test subject lying within the first sub-region of the first latent trait as a prior second sub-region probability for the second latent trait. The second latent trait may be a psychiatric disorder, such as generalized anxiety disorder. In this regard, the first latent trait may be, for example, depression.

In another aspect, the initial first sub-region probability of the test subject lying within the first sub-region of the first latent trait is determined before receiving the subsequent first test item from the test subject.

In another embodiment, a method for assessing a latent trait in a test subject is provided. The method may include the step of administering a test item from a plurality of first test items to a test subject to elicit a response to the first test item from the test subject. The administering may occur, for example, through a GUI. The method also includes determining sub-region probabilities of the test subject lying within each of a plurality of sub-regions of a first latent trait from the test subject response to the first test item. The method may also include determining a differential probability value between at least first and second adjacent sub-regions of the first latent trait. These steps may be repeated until the differential probability value between the first and second sub-regions is a terminus differential probability value that meets or exceeds a threshold differential probability value.

In one aspect, the method further includes determining a severity score for the first latent trait in a test subject from the terminus differential probability value. The severity score for the first latent trait may be determined by mapping the terminus differential probability value to a severity score validated evidence data set.

In another aspect, the step of determining the sub-region probabilities of the test subject lying within each of the plurality of sub-regions of first latent trait comprises determining the sub-region probabilities using: (i) the test subject's response to the test item to determine a conditional sub-region probability; and (ii) a previously determined sub-region probability of the test subject lying within each of the plurality of sub-regions of the first latent trait as a prior sub-region probability.

In another aspect, the sub-region and probabilities are determined using Bayesian inferences. The first latent trait may be a psychiatric disorder, such as depression.

In another aspect, the sub-region probabilities of the test subject lying within each of the plurality of sub-region of the first latent trait are normalized to one before determining a differential probability value. In another aspect, the plurality of first test items includes agreement test items that elicit the test subject to indicate a level of agreement of disagreement with a concept. The agreement test items may elicit a level of agreement on a Likert scale. In another aspect, the plurality of first test items may include physiological test items that elicit the test subject to indicate the presence or absence of a physiological condition.

In another embodiment, a method for creating a validated evidence probability data set is provided. The validated evidence probability data set includes conditional response probabilities and response probabilities for at least a first latent trait. The method may include selecting a plurality of test items, administering the plurality of test items to a first test subject, and recording the first test subject's responses to the plurality of test items. The recording may occur, for example, using a GUI operatively coupled to a computer-readable storage medium. The method may further include inputting a criterion measurement of each sub-region of a first latent trait in the first test subject. For example, the criterion measurement may be determined by a clinical evaluation of the first test subject (e.g., by a psychologist or psychiatrist). The method may also include administering a plurality of test items to a subsequent test subject and recording the subsequent test subject's responses to the plurality of test items. A criterion measurement of each sub-region of a first latent trait in the subsequent test subject may also be input. The steps of administering, recording and inputting for subsequent test subjects may be repeated as necessary to create a validated evidence data set. Thereafter, for each possible response to a test item, a conditional response probability may be determined within each sub-region of the first latent trait and response probabilities may be determined for each response across the first latent trait to create a validated evidence probability data set.

In one aspect, the step of selecting a plurality of test items may include selecting existing test items used in existing test protocols. In another aspect, the step of selecting a plurality of test items may include selecting test items that are created by an expert in the field of the first latent trait. The step of administering the plurality of test items may include administering the test items on a paper form to the test subject. In another aspect, the step of administering the plurality of test items includes administering the test items through a GUI.

In another aspect, the criterion measurements are determined by a psychologist or by psychiatrist. In yet another aspect, the determining steps are performed using Bayesian inferences.

The first latent trait may be a psychiatric disorder, such as depression. In another aspect, the inputting steps include inputting the criterion measurement of each sub-region of a second latent trait in the test subjects. In yet another aspect, the method further includes the step of determining apriori sub-region probabilities for the sub-regions of the first latent trait. In a further refinement of this aspect, the method may include determining the apriori sub-region probabilities of the second latent trait using the apriori sub-region probabilities of the first latent trait.

In another embodiment, a method for creating a psychometric measurement instrument protocol comprising a plurality of test items to be administered to a test subject to assess at least a first latent trait in the test subject is provided. The method may include the steps of loading a plurality of test items and a validated evidence probability data set associated with the plurality of test items into a database, e.g., on a computer-readable storage medium, where the test items are relevant to a first latent trait. The test items may be sequentially ordered in a first test item sequence. Thereafter, the accuracy of the first test item sequence may be determined using the validated evidence probability data set. Thereafter, the plurality of test items may be sequentially ordered in a subsequent test item sequence that is different than the first item sequence and the accuracy of the subsequent test item sequence may be determined using the validated evidence probability data set. The steps may be repeated for further subsequent test item sequences. Thereafter, a test item sequence may be selected and administered to a test subject to assess the first latent trait in the test subject.

In another embodiment, an apparatus for assessing a latent trait in a test subject is provided. The apparatus may include a GUI configured to display a plurality of first test items to a test subject to elicit and receive the test subject's first test item responses to the plurality of first test items. A computer readable storage medium is operatively coupled to a processor, the computer readable storage medium storing one or more sequences of instructions which, when executed by one or more processors, causes the one or more processors to: (i) determine an initial first sub-region probability of the test subject lying within a first sub-region of a first latent trait from the test subject's response to the initial first test item; and (ii) determine a subsequent first sub-region probability of the test subject lying within the first sub-region of the first latent trait using the test subject's response to the subsequent first test item to ascertain a conditional response probability, and using the initial first sub-region probability as a prior first sub-region probability.

In another embodiment, a computer readable storage medium is provided that stores one or more sequences of instructions which, when executed by one or more processors, causes the one or more processors to execute the steps of receiving a test subject's first test item responses to a plurality of first test items that are administered to the test subject to elicit the first test item response from the test subject, determining an initial first sub-region probability of the test subject lying within a first sub-region of a first latent trait from the test subject's response to the initial first test item, and determining a subsequent first sub-region probability of the test subject lying within the first sub-region of the first latent trait using the test subject's response to the subsequent test item to ascertain a conditional response probability, and the initial first sub-region probability as a prior first sub-region probability.

DESCRIPTION OF THE DRAWINGS

FIG. 13 illustrates a block diagram of a network system for implementing the methods described herein.

DESCRIPTION OF THE INVENTION

Figure 1:
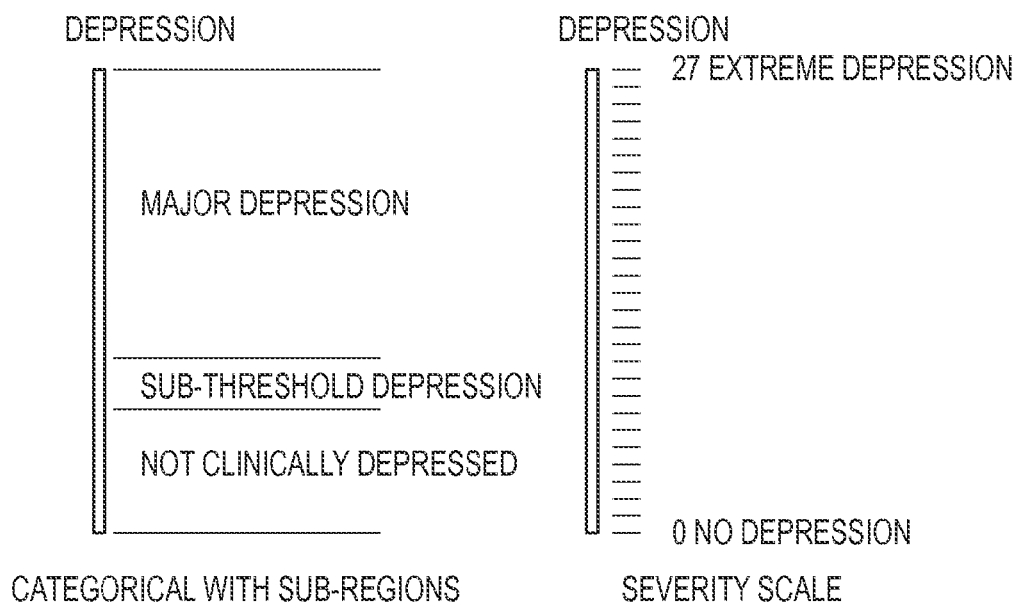
FIG. 1 illustrates two alternate examples of the representation of the classification of the latent trait depression.

In one aspect, the present invention relates to psychometric measurement instruments and methods for assessing latent traits in a test subject (e.g., a patient seeking treatment) that utilize probabilistic scoring of psychometric measurements to increase accuracy of the assessment and/or decrease the time required to reach a result. A latent trait is a construct representing, for example, a test subject's intelligence, abilities, attitudes, personality traits, or a psychiatric condition such as a psychiatric disorder. In this regard, psychiatric disorders that may be assessed using the measurement instruments and methods described herein may include, but are not limited to, depression, dysthymic disorder, bipolar disorder, generalized anxiety disorder, obsessive-compulsive disorder, post-traumatic stress disorder (PTSD), psychotic disorders, personality disorders, sleeping disorders, eating disorders, developmental disorders and substance dependencies (e.g., drug dependencies). Although the following description is directed primarily to the assessment of psychiatric disorders in test subjects, the measurement instruments and methods may also be utilized in, for example: intelligence and aptitude testing such as for employment screening or evaluating students; assessing legal competency such as in a legal proceeding; assessing personality traits and the like.

The methods may generally include administering a plurality of test items (e.g., sequentially) to a test subject to elicit a test item response from the test subject to each of the test items. The responses serve as the basis for assessing the latent trait(s). The test items may include, for example: multiple-choice questions, including factual-based questions (e.g., regarding sex, race or age of the test subject); true/false questions; questions or statements that elicit test subject to indicate a level of agreement or disagreement (e.g., on a Likert scale), referred to herein as "agreement test items"; or questions or statements that elicit a test subject to indicate the presence or absence of a symptom, such as a physiological condition, and possibly indicating how often the condition is experienced referred to herein as "physiological test items."

The test items may be administered to a test subject orally or in writing, and the responses recorded on a form (e.g., a paper form) filled out manually (e.g., using a pencil or pen) by the subject or by a person administering the test items to the test subject. The test subject's response to each of the test items may also be recorded electronically as the test items are sequentially administered to the test subject such as through a graphical user interference (GUI). In this regard, the methods may be implemented using an electronic device (e.g., a computing device) such as one that includes one or more processor (e.g., a microprocessor) that is operatively coupled to a computer-readable data storage medium. For example, the methods may be embodied in a portable interactive device similar to that described by U.S. Pat. No. 5,572,421 by Altman et al., which incorporated herein by reference in its entirety. Another example of a portable interactive electronic device is sold by Patient Tools, Inc. of Littleton, Colo. The test items may also be administered to a test subject (or reported by another person) over a client device such as a desktop computer, a laptop computer, a mobile telephone device, a PDA, a Smartphone, an I-Pad or other computing tablet, or the like. Such a client device may include, for example, an internet browser application (e.g., a Microsoft Internet Explorer or the like) for providing a communication interface with a network (e.g., a local area network or a wide area network) and for displaying graphical user interfaces (GUIs) such as for eliciting responses from the test subject. In any event, the test subject's responses to the test items may advantageously be electronically recorded and processed (e.g., analyzed) as the test items are administered to permit dynamic probabilistic scoring, or may be uploaded to a database (e.g., a remote database) at a later time.

Latent traits such as depression can be expressed as a severity continuum with sub-regions (e.g., exclusive sub-regions) along the continuum. With reference to FIG. 1, the latent trait of depression is expressed in two related manners. On the right side of FIG. 1, depression is numerically represented on a severity scale of to 27, as would result from the administration of a PHQ-9 measurement instrument. The PHQ-9 measurement instrument administers nine test items to a test subject. Each of the test items is in the form of a question asking the test subject how often they have been bothered by a problem over a specified time period preceding the administration of the test (e.g., "How often have you been bothered by poor appetite or over eating in the past two weeks?"). The test subject responds by selecting one of four response options, each of which is associated with a numerical value from 0 to 3. For example, selecting the response "not at all" correlates to a score of 0, whereas the response "nearly every day" correlates to a score of 3. At the conclusion, the numerical values are summed and the total severity score is output. Thus, a severity score of 0 indicates no depression, whereas a severity score of 27 indicates extreme depression. A numerical severity score continuum lies between these two points.

On the left side of FIG. 1, depression is expressed as lying in one of three mutually exclusive sub-regions of the trait, namely "Not Clinically Depressed", "Sub-Threshold Depression" and "Major Depression." The sub-region Not Clinically Depressed corresponds to a PHQ-9 severity score of 0 to 6, Sub-Threshold Depression corresponds to a PHQ-9 severity score of 7 to 9, and Major Depression corresponds to a PHQ-9 severity score of 10 or higher.

The measurement instruments and methods disclosed herein may include a determination of the conditional probability that the test subject is located within a particular sub-region of a latent trait based upon the test subject's responses to the test items associated with the latent trait (referred to herein as a "sub-region probability" for the latent trait). For example, given the test subject's response to a test item (e.g., an initial test item), the conditional probability that the test subject lies within each of a plurality of sub-regions across the latent trait continuum can be determined. This determination may be made by using the conditional probability of receiving that response from a test subject lying within the sub-region (referred to herein as the "conditional response probability" for the latent trait). The conditional response probability may be determined, for example, from a validated evidence probability data set. These sub-region probabilities may then be refined and updated using the test subject's response(s) to one or more subsequent test items, such as by using the previously determined sub-region probabilities (e.g., the most recent sub-region probability determinations) as prior sub-region probabilities and by using the conditional response probability for the subsequent test items.

Test items may be sequentially administered to the test subject and probability scoring applied after each test item is processed until one of the latent trait sub-region probabilities (e.g., a terminus sub-region probability) is determined that meets or exceeds a predetermined threshold probability value such that the administration of the test items to the test subject may be terminated and the latent trait sub-region with the highest sub-region probability may be output as a result. Alternatively, all test items from a test protocol may be administered to the test subject (e.g., on a paper form) and the responses input (e.g., into a computer data base) for assessment. In addition, or in lieu of, differential probability values between adjacent sub-regions of a latent trait may also be determined. Differential probability values represent the difference between the sub-region probability of a first sub-region and the sub-region probability of an adjacent second sub-region. Once a differential probability value (e.g., a terminus differential probability value) is determined that meets or exceeds a predetermined threshold probability value, the administration of test items may be terminated. The differential probability values may be used to estimate a severity score for the test subject, as well as to determine when the administration of test items can be terminated with an acceptable pre-determined loss in accuracy (e.g., as compared to administering further test items).

As is noted above, latent trait sub-region probabilities may be determined by comparing the test subject's response to a validated evidence probability data set that includes the conditional probability of receiving that response to the test item when the latent trait sub-region is present (i.e., the conditional response probability). The validated evidence probability data set may be a data set that has been validated by a trained professional (e.g., a psychologist or psychiatrist) making a criterion measurement of the concept. That is, a validated evidence data set may be produced by comparing the test item responses from a large number of test subjects (e.g., a statistically significant number of test subjects) to a trained professional's measurement of the concept (e.g., depression) in those test subjects. From the validated evidence data set, the probabilities that a test subject will submit that response when the test subject lies within each of the sub-regions of that latent trait can be determined to create a validated evidence probability data set. Thus, the validated evidence probability data set may provide the conditional probability of seeing a test subject's response to a particular test item assuming the test subject lies within a given sub-region of the latent trait, and also the probability of seeing the test subject's response for all sub-regions of the latent trait (the latter referred to herein as "the latent trait response probability").

The measurement instruments and methods may include the iterative use of both conditional response probabilities and prior sub-region probabilities to determine the latent trait sub-region probabilities to a high degree of accuracy. The use of conditional response probabilities advantageously exploits the concept that the statistical evidence from a response to a test item will change the probability of a test subject lying within a sub-region of a latent trait, i.e., will change the latent trait sub-region probability. Accordingly, the latent trait sub-region probability may be determined by optionally starting with an apriori probability of the test subject lying within the sub-region (e.g., from one or more validated evidence data sets of a general population to which the test subject belongs) and successively determining a refined and updated sub-region probability given the response to each test item that is administered, and by using the prior sub-region probability (e.g., determined from a prior response to a test item) in the refined determination.

The sub-region probabilities may be determined using validated evidence probability data sets by applying methodologies such as logistic regression or likelihood ratios. In one embodiment, the sub-region probabilities are determined by applying Bayesian inferences. Baye's Theorem states that the conditional probability of a concept (e.g., the test subject lying in a particular latent trait sub-region) given some evidence (e.g., the test subject's response to a test item) is equal to the conditional probability of receiving the evidence given the presence of the concept, times the probability of the concept, divided by the probability of the evidence. As applied to psychometric measurement of a latent trait, the conditional sub-region probability given the test subject's response to a test item is a function of the conditional probability of receiving that response from a test subject lying in that sub-region in a validated evidence probability data set, the probability of seeing that response in the validated evidence probability data set (i.e., across all sub-regions), and the prior sub-region probability before seeing the new test item response.

The Bayesian inference method can be represented by the following equation:

$$p(C|E) = \frac{p(E|C) \cdot p(C)}{p(E)}$$

As applied to the psychometric measurement instruments and methods described herein, the concept C is the test subject lying within a specific latent trait sub-region and the evidence E is the specific response to a test item. Thus, $p(C|E)$ is the (conditional) latent trait sub-region probability, $p(E|C)$ is the conditional response probability from a validated evidence probability data set, $p(C)$ is the prior sub-region probability and $p(E)$ is the latent trait response probability, i.e., across all sub-regions of the latent trait, also from a validated evidence probability data set.

Using an iterative process, the prior sub-region probability $p(C)$ may be the sub-region probability determined before the response to the subsequent test item is input.

In practice, because the latent trait sub-regions are mutually exclusive, the sub-region probabilities of all sub-regions of a latent trait may be determined and scaled so that the total probability of all the sub-regions for the latent trait equals one. The iterative process may be applied for all test items administered and the sub-region with the highest resulting sub-region probability may be selected and output as the result for that test subject.

Figure 2:
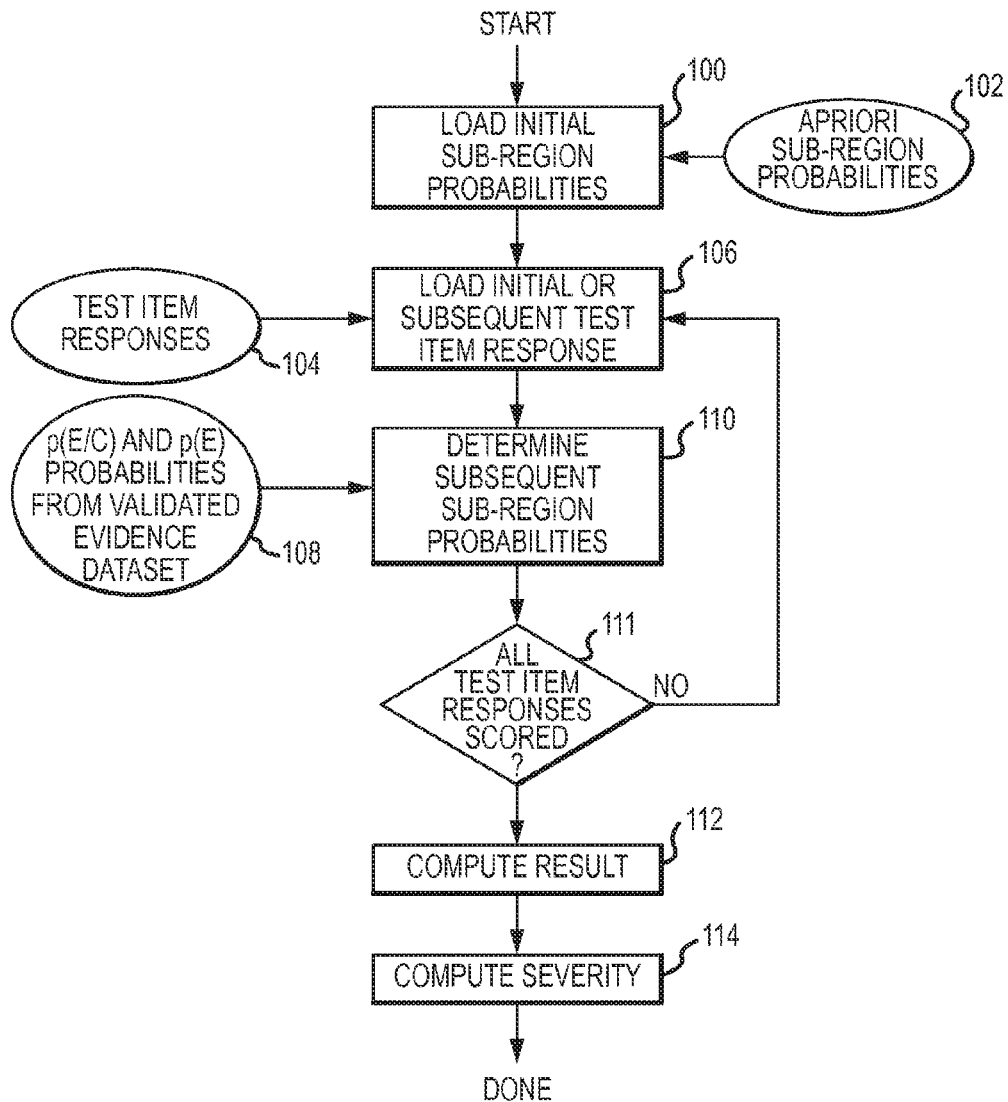
FIG. 2 illustrates a flowchart of an exemplary method for probabilistic scoring to assess a latent trait.

FIG. 2 illustrates a flow chart of an exemplary method for assessing a latent trait in a test subject. At step 100, the initial set of sub-region probabilities may simply be set equal or be extracted from one or more apriori data sets 102 to be used as prior probabilities. That is, the determination of the initial sub-region probabilities may use apriori validated evidence data from a general population as a prior probability, if the apriori probability data set 102 is available. For example, it may be known from validated evidence that a test subject from a particular race, sex, geographic location, etc. . . . has an apriori probability for each of the sub-regions across a latent trait.

At step 106 a test item response (e.g., an initial test item response) from a plurality of test item responses 104 is received from (e.g., is extracted from) the test item responses 104. As is noted above, the test items that generate the responses 104 may include multiple-choice questions, true/false questions, questions or statements that indicate a level of agreement or disagreement, questions indicating the presence or absence of a symptom, and the like. The test items may be administered on paper or administered electronically though a GUI on a computing device, such as one having a GUI for administering (e.g., displaying) the test items and eliciting responses from the test subject to the test items.

At step 110, subsequent sub-region probabilities for the latent trait are determined. The subsequent sub-region probabilities may be determined using: (i) the test subject's response to the test item received at step 106; (ii) the conditional response probability $p(E/C)$ and response probability $p(E)$ from a validated evidence probability data set 108; and (iii) as prior sub-region probabilities $p(C)$, the sub-region probabilities initially loaded at step 100, or resulting from a previous execution of step 110. That is, the test subject's response is used to select the associated evidence probabilities from a validated evidence probability data set 108 to ascertain the new sub-region probabilities given the response. The validated evidence probability data set 108 may comprise data extracted from a general population, e.g., across all races, ethnicities, etc. Alternatively, a more accurate result may be obtained if the validated evidence probability data set 108 is created from a subset of data that is associated with the test subject. For example, the validated probability data set 108 may comprise data only for a particular ethnic background where cultural perception of mental health and normal behavior may be different from other ethnic backgrounds. Further, validated probability data set 108 may comprise data from a single sex or a single race, for example, to which the test subject belongs.

After determination of the subsequent sub-region probabilities at step 110, the set of previously administered test item responses 104 can be checked to see if all the test items have been processed. If not, the process may go back to step 106 for further refinement of the sub-region probabilities at step 110. When all the test items have been processed, the result (i.e., in which sub-region the test subject is located) may be determined at step 112, and the severity (i.e., the test subject's position along the latent trait) may be determined at step 114.

Figure 3:
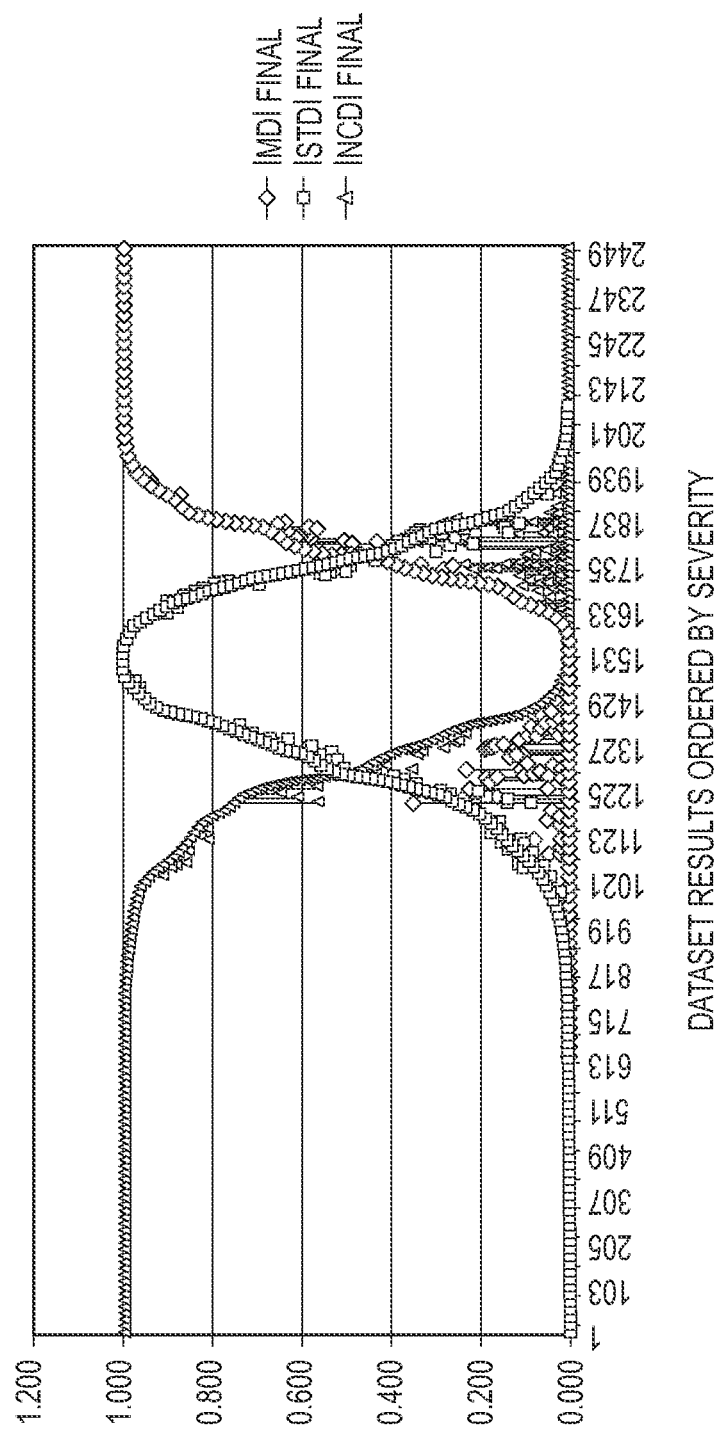
FIG. 3 illustrates an example of sub-region probabilities to assess a latent trait.

As an illustration of this probabilistic scoring methodology, in FIG. 3 a PHQ-9 validated evidence data set comprising data from about 2500 test subjects is used to compute the sub-region probabilities of Major Depression (MD), Sub-Threshold Depression (STD) and Not Clinically Depressed (NCD) for every test case in the data set (e.g., application of all the steps in the flowchart of FIG. 2 leading up to step 112). The test cases are ordered by their computed severity (explained below) from lowest to highest severity and the resulting sub-region probabilities are graphed in FIG. 3. This illustrates how the sub-region probabilities vary across the depression latent trait continuum. As would be expected, of the approximately 2500 cases in the data set, the probability of NCD is effectively one (e.g., 100%) for the first (less severe) cases, the probability of STD rises to effectively one for several hundred cases in the middle and the probability of MD rises to effectively one for about the final 500 (more severe) cases.

Figure 4:
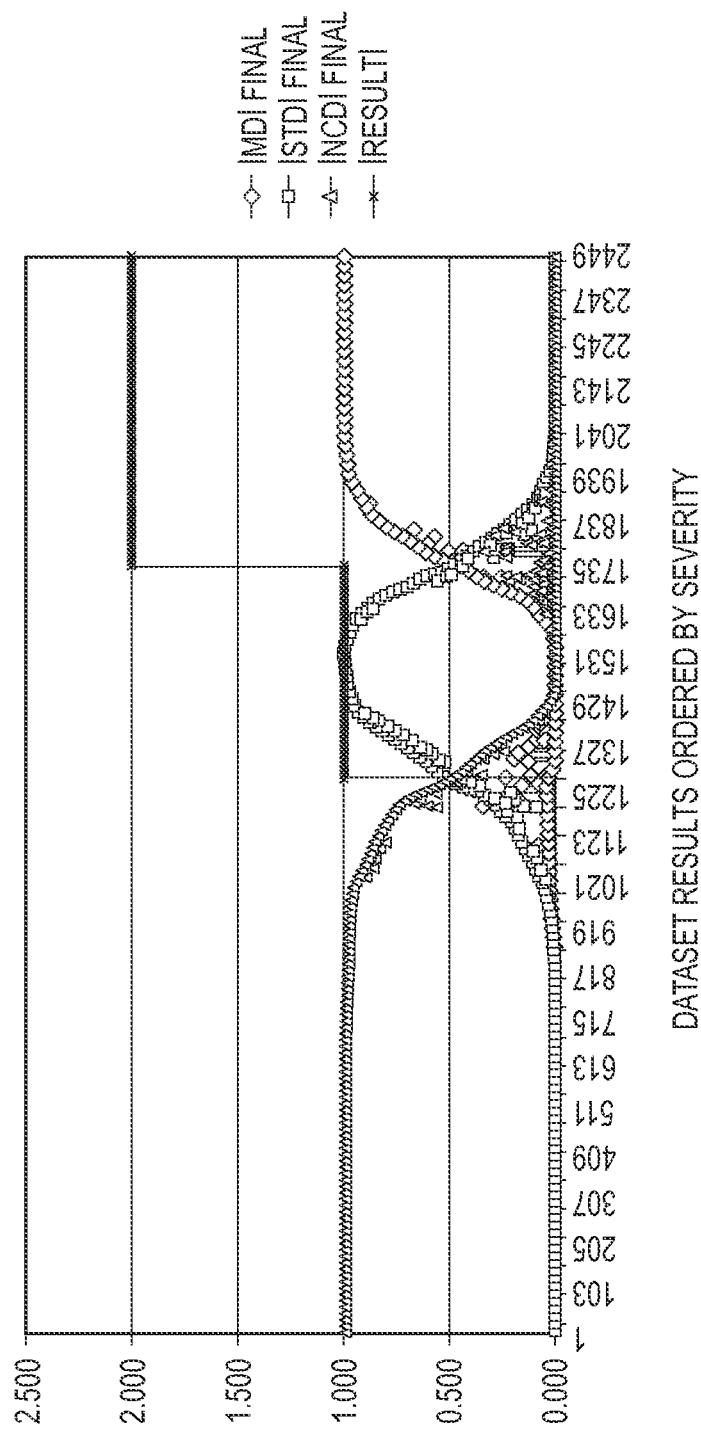
FIG. 4 illustrates an example of determining a sub-region with the largest conditional probability.

In FIG. 4 the selection of the sub-region with the highest resulting sub-region probability as the result to be output is applied (e.g., step 112 in the flowchart of FIG. 2). NCD is assigned the value of zero, STD is assigned the value of one and MD is assigned the value of two. The borders between latent trait sub-regions are clearly marked by the probability curves for adjacent sub-regions crossing over each other, low to high or high to low.

At step 114 in the flowchart of FIG. 2, the severity of the latent trait may be determined for a test subject from the resulting sub-region probabilities. One method could be to simply report all the sub-region probabilities. Another method could be to subtract the sub-region probabilities between adjacent sub-regions to obtain a differential probability value. The differential probability value may be shifted, scaled and/or mapped to match linear or other desired severity scales (e.g., the PHQ-9 severity scale). When more than two sub-regions exist, logic could first be used to determine which differential probability value to apply.

Figure 5:
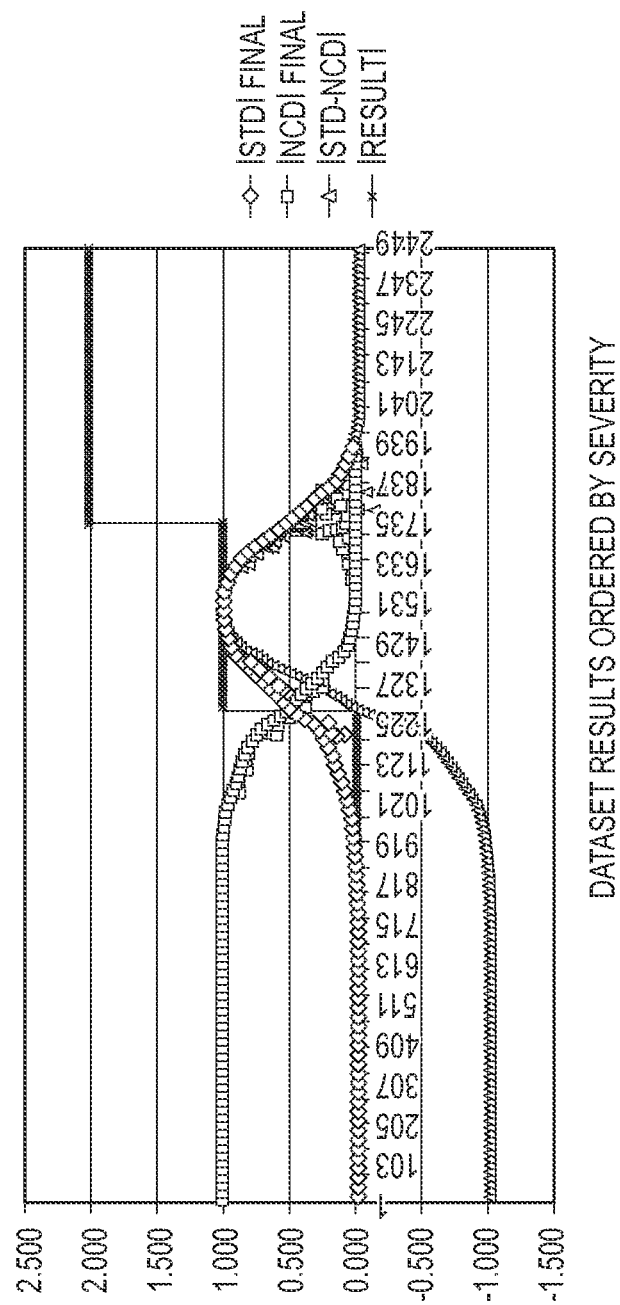
FIG. 5 illustrates an example of determining differential probability values between adjacent sub-regions.

As an illustration of this severity scoring methodology, in FIG. 5 the STD-NCD differential probability value, found by subtracting the sub-region probability of NCD from the sub-region probability of STD, has been added to the PHQ-9 data set results from FIG. 4. The STD-NCD differential probability value starts at minus one for the least severe cases, rises to one in the middle of the STD sub-region, and goes to zero for the most severe cases in the MD sub-region.

Figure 6:
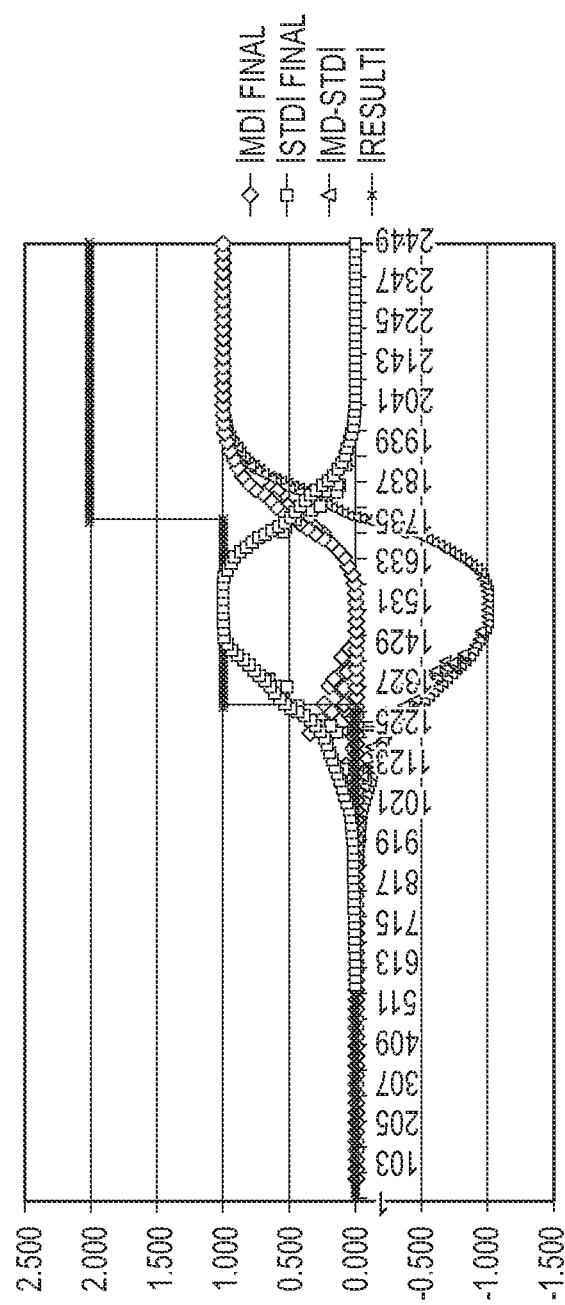
FIG. 6 illustrates an example of determining differential probability values between adjacent sub-regions.

Conversely, in FIG. 6 the MD-STD differential probability value found by subtracting the sub-region probability of STD from the sub-region probability of MD, has been added to the PHQ-9 data set results from FIG. 4. The MD-STD differential probability value starts at zero, goes down to minus one in the middle of the STD sub-region, and rises to one in the MD sub-region.

Figure 7:
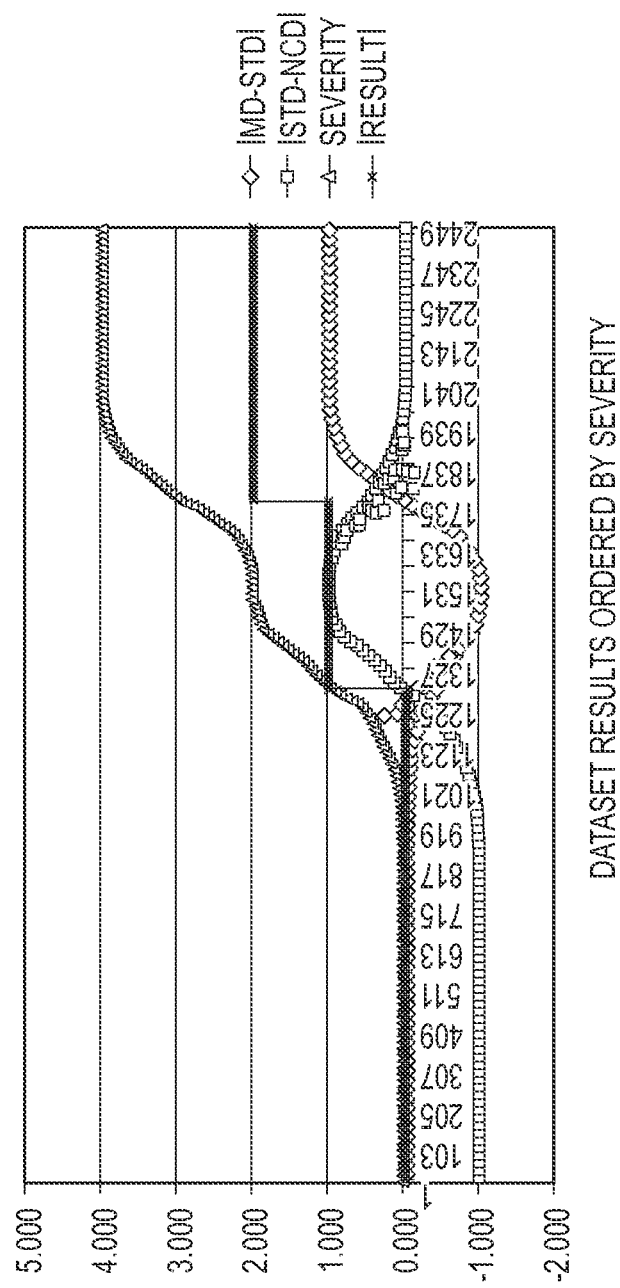
FIG. 7 illustrates an example of determining latent trait severity from differential probability values.

FIG. 7 illustrates that when a sub-region (e.g., STD) has two adjacent sub-regions, the adjacent sub-region probability values may be subtracted (e.g., most severe minus less severe) and the result may be used to determine which differential probability value to use to determine severity. Specifically, the NCD sub-region only has an adjacent STD sub-region so the STD-NCD differential probability value (e.g., FIG. 3) is applied. In the STD sub-region, when the adjacent MD sub-region probability is subtracted from the adjacent NCD sub-region probability and the result is positive (i.e., the first half of the STD sub-region), then the STD-NCD differential probability value is applied, otherwise the MD-STD differential probability value is applied. The MD sub-region only has the STD adjacent sub-region so the MD-STD differential probability is applied. To obtain a severity score the STD-NCD differential probability value is shifted up one (add one to the score) and the MD-STD differential probability is shifted up three (add three to the score). If subsequent sub-regions existed, they would be shifted up five, seven, etc. The resulting severity scores plotted over the full continuum of the depression latent trait produces a curve that is relatively flat in the middle of a sub-region and changes quickly over the transition between adjacent sub-regions, showing the desired characteristic of a high sensitivity to change, particularly at the transitions between adjacent sub-regions of a latent trait.

Figure 8:
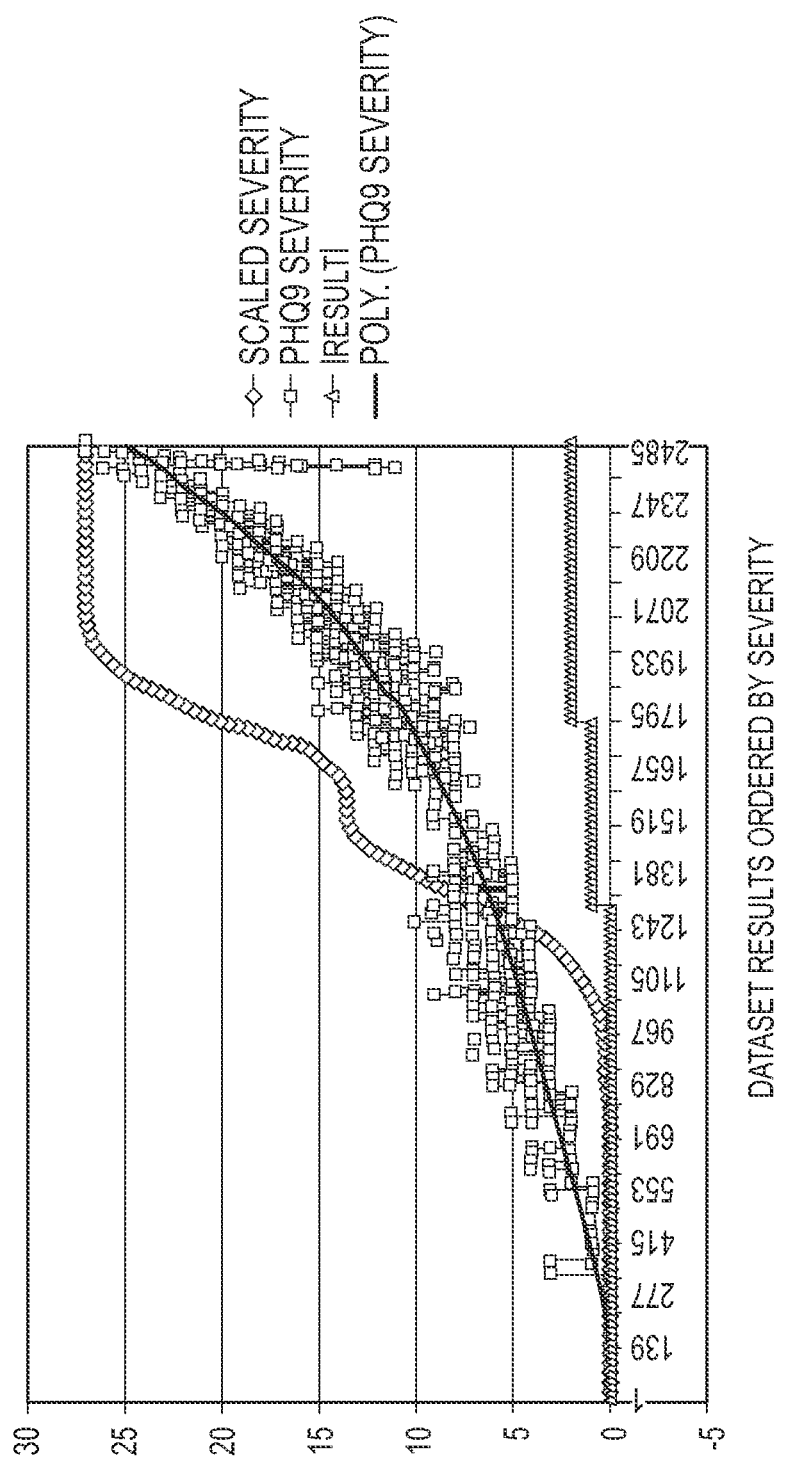
FIG. 8 illustrates an example of mapping latent trait severity to a different desired severity scale.

In FIG. 8, the severity score curve from FIG. 7 is scaled (i.e., multiply the severity score from FIG. 7 by 27 and divide by 4) to match the PHQ-9 hand scored severity with a maximum value of 27. In addition, the original PHQ-9 hand scored severity values are plotted for each case with a polynomial best fit curve plotted through the distribution of hand scored values. A lookup table mapping from computed and scaled severity to an estimate of the original PHQ-9 hand scored severity (the polynomial best fit curve) can be generated. A mapping to a linear severity scale across the depression latent trait continuum, or any other desired scale, can be produced using this methodology.

When a latent trait assessment is administered electronically, the probabilistic method for determining sub-region probability and/or severity discussed above can be performed in real-time immediately after each test item response is received and processed. Additionally, since all of the sub-region probabilities are known at all times during the assessment (e.g., from the validated evidence probability data sets), the assessment process can be terminated at any time, based on a termination condition, and the result and/or severity can be determined as outlined above. Termination conditions may include reaching a desired level of accuracy (sensitivity and specificity), with the termination condition being when a test subject is known to be located within a specific sub-region. Methods for determining a test subject being located in a sub-region may include when a sub-region probability reaches or exceeds a minimum threshold sub-region probability or when the differential probability value between sub-regions meets or exceeds a threshold differential probability value threshold.

Figure 9:
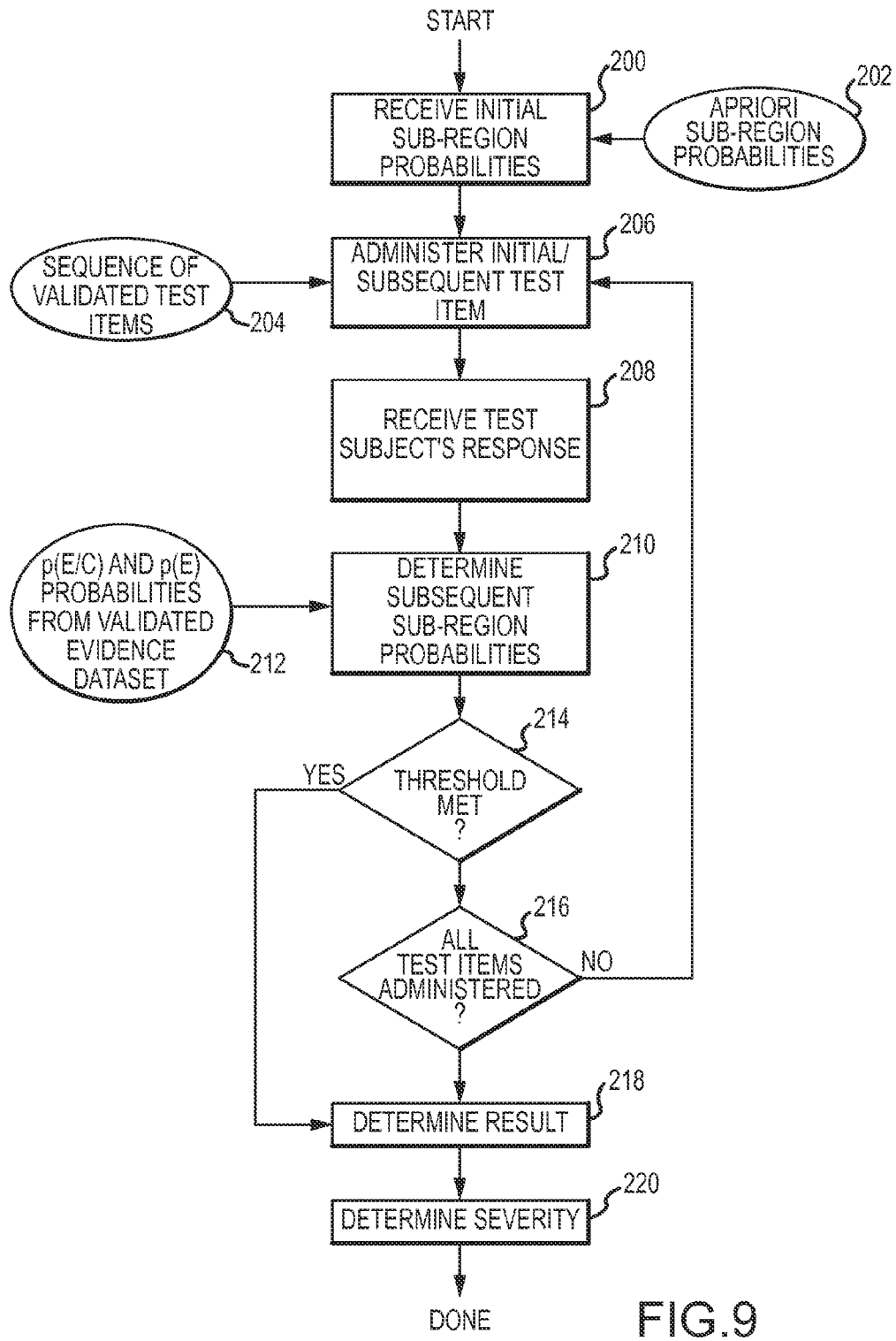
FIG. 9 illustrates a flowchart of an exemplary method for assessing a latent trait using probabilistic scoring.

FIG. 9 illustrates a flow chart of an exemplary method for dynamically assessing a latent trait using probabilistic scoring. The process is substantially similar to that illustrated in FIG. 2 with the prior sub-region probabilities being received at step 200 from an apriori validated evidence data set 202. At step 206 a test item selected from a sequence of validated test items 204 is administered to the test subject. At step 208 the test subject's response is recorded and at step 210 the subsequent sub-region probabilities are determined from the validated evidence probability data set 212 using the test subject's response recorded at step 208.

At step 214 the termination condition of a threshold being met is determined (e.g., a threshold sub-region probability or threshold differential probability value) and if yes, then the processing moves forward to determining the result at step 218 and/or the severity at step 220. If the termination condition has not been met, then processing proceeds to step 216 to determine if all the test items in the sequence have been administered. If all the test items have not been administered, processing may go back to step 206 to administer the next test item to the test subject. If all the test items have been administered then processing may proceed to determining the result at step 218 and/or severity at step 220.

An advantage of terminating the administration of test items early (e.g., at step 214) is that less questions on average need to be administered, saving time for the test subject and the physician. Similar to the probabilistic scoring methodology described above (FIGS. 3 through 8) where the results for a test subject are determined using the validated evidence probability data set, simulations can also be run using the validated evidence probability data set to determine the accuracy (e.g., sensitivity and specificity) and the average number of test items required for a particular sequence of test items when a specific threshold probability (sub-region or differential) is desired. This is described in more detail below with respect to FIG. 12.

Figure 10:
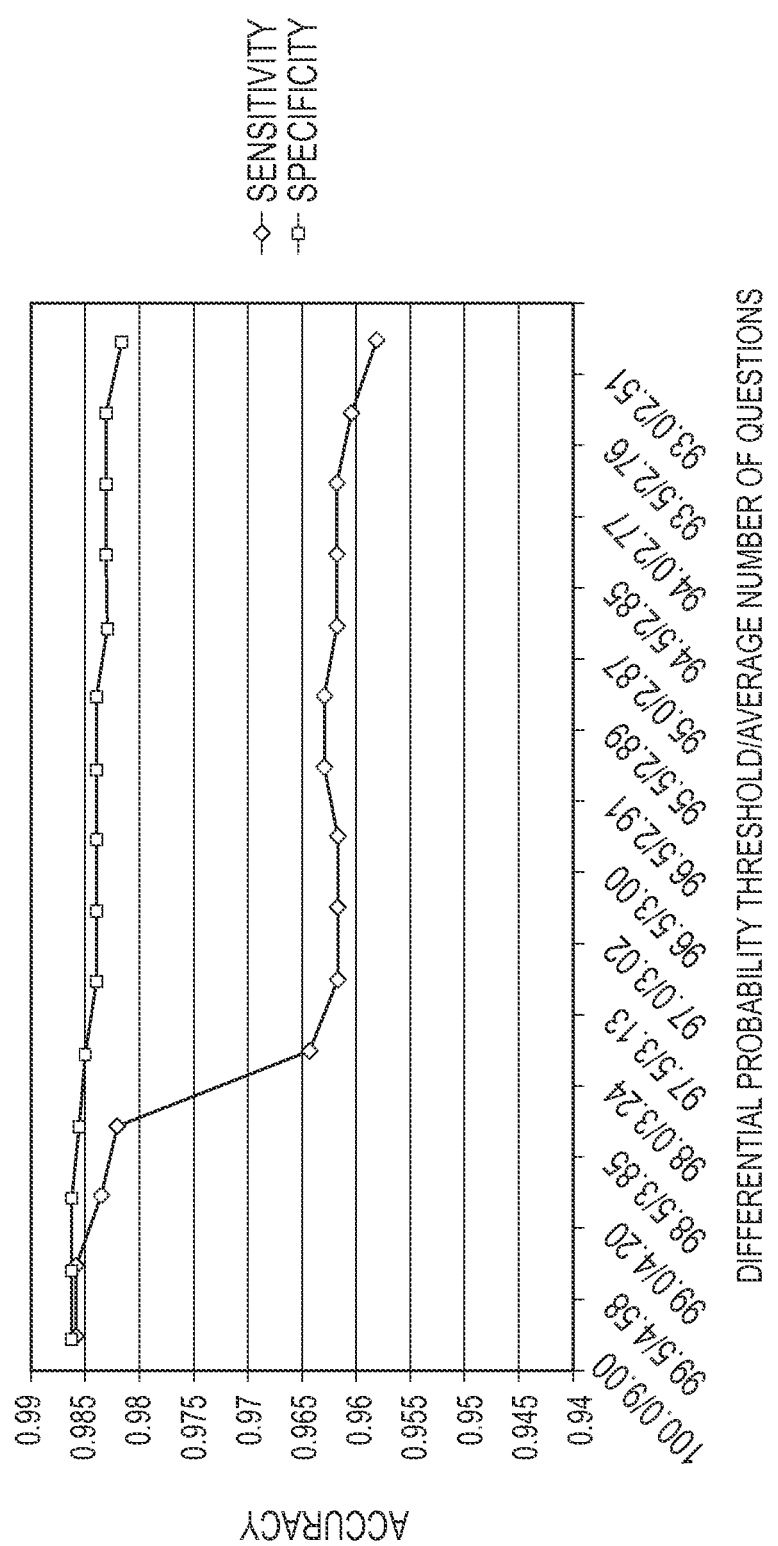
FIG. 10 illustrates a plot of latent trait measurement accuracy versus number of administered test items.

As an illustration of this tradeoff between accuracy and number of test items administered, FIG. 10 shows an example of the simulation results for different differential probability threshold values using a PHQ-9 validated evidence data set where the criterion measure is the hand scored result, i.e., by a trained professional. By utilizing the probabilistic determination methods described herein, there is effectively little to no loss in accuracy if a differential probability value threshold of 98.5% is used, which results in only about four test items being administered to the test subject on average. This equates to about a 55% reduction in the average time required to administer the measurement instrument.

Utilizing the foregoing methodology, the accuracy of the measurement instrument can be greatly increased compared to hand scoring, and/or the number of test items administered to a test subject can be reduced. Stated another way, more information can be collected in a shorter amount of time.

The probabilistic scoring and dynamic assessment may also be utilized to assess more than one latent trait in a test subject at a time. For example, after the administration of test items for a first latent trait is terminated and a sub-region of that first latent trait is determined as a result, a similar methodology can be utilized to assess a second latent trait. In this regard, the first latent trait sub-region can be utilized to ascertain the (conditional) apriori probability for the second latent trait from a validated probability evidence data set. By using a conditional probability ascertained based on the sub-region of the first latent trait, the accuracy of the result for the second latent trait sub-region can be greatly increased, and/or the time required (e.g. the number of test items administered to the test subject) to identify the sub-region and/or severity for the second latent trait can be greatly reduced.

Figure 11:
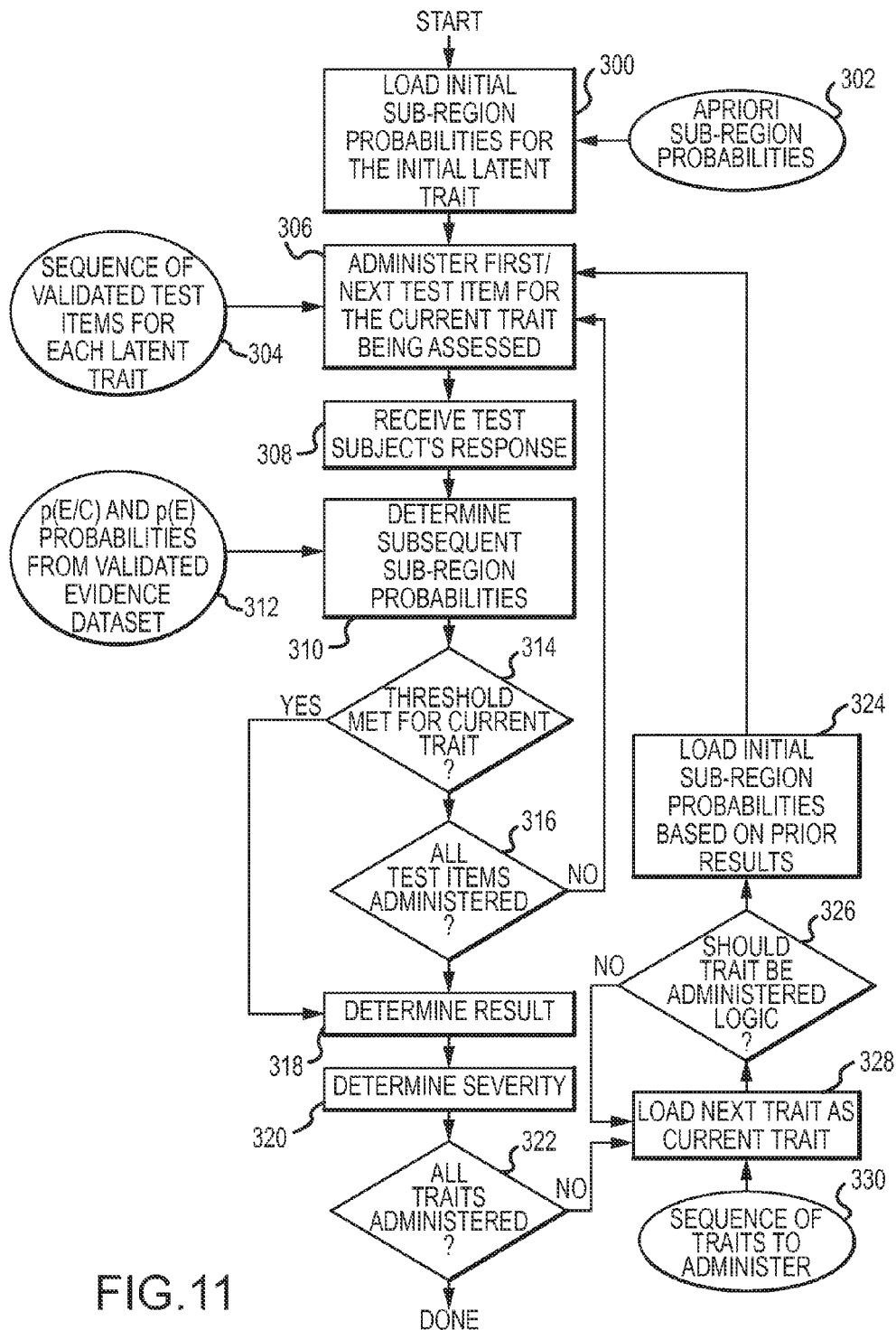
FIG. 11 illustrates a flowchart of an exemplary method for assessing multiple latent traits using probabilistic scoring.

FIG. 11 illustrates a flow chart of an exemplary method for dynamically assessing multiple latent traits using probabilistic scoring. The process is substantially similar to that illustrated in FIG. 9 with the prior sub-region probabilities being loaded at step 300 from an apriori validated probability evidence data set 302. At step 306 a test item selected from a sequence of validated test items for the latent trait currently being assessed 304 is administered to the test subject. At step 308 the test subject's response is received and at step 310 the subsequent sub-region probabilities are determined from the conditional response probabilities and response probabilities 312 for the test subject's response.

At step 314 the termination condition of a threshold being met (e.g., threshold sub-region probability or threshold differential probability value) is determined and if yes, then the processing moves forward to determining the result at step 318 and/or the severity at step 320. If the termination condition has not been met, then processing proceeds to step 316 to determine if all the test items in the sequence have been administered. If all the test items have not been administered, processing goes back to step 306 to administer the next test item. If all the test items have been administered then processing proceeds to determining the result at step 318 and/or the severity at step 320.

At step 322 the sequence of latent traits to administer 330 is checked to see if all the latent traits have been assessed. If not, processing proceeds to step 328 where the next latent trait is loaded as the current trait. In step 326 logic can be applied as to whether the new current latent trait should be administered. This logic could include triggers from pre-loaded configurations or triggers from prior sub-region probabilities exceeding a threshold. In step 324, the prior sub-region probabilities for the current latent trait are determined and loaded from prior results. Execution then continues at step 306 assessing the new current latent trait. The sequence may be repeated for any number of latent traits in a test subject.

The measurement instruments and methods described herein may utilize test items (e.g., test items 104, 204 and 304) selected from a pool of available test items. In this regard, the administration of test items may follow a known protocol such as the PHQ-9. That is, the methods can administer the PHQ-9 questions sequentially and use probabilistic scoring and thresholds to terminate the administration of the PHQ-9 before all 9 questions are administered. Effectively any existing assessment (CES-D, Zung, GAD-7, etc.) can be converted to use probabilistic scoring (theoretically producing higher accuracy than hand scoring) and/or converted to being administered dynamically (requiring less questions on average). Alternatively, the simulator functionality used in FIG. 10 to determine accuracy and average number of questions required, could be expanded to select and order new protocols of test items designed to assess specific latent traits.

Figure 12:
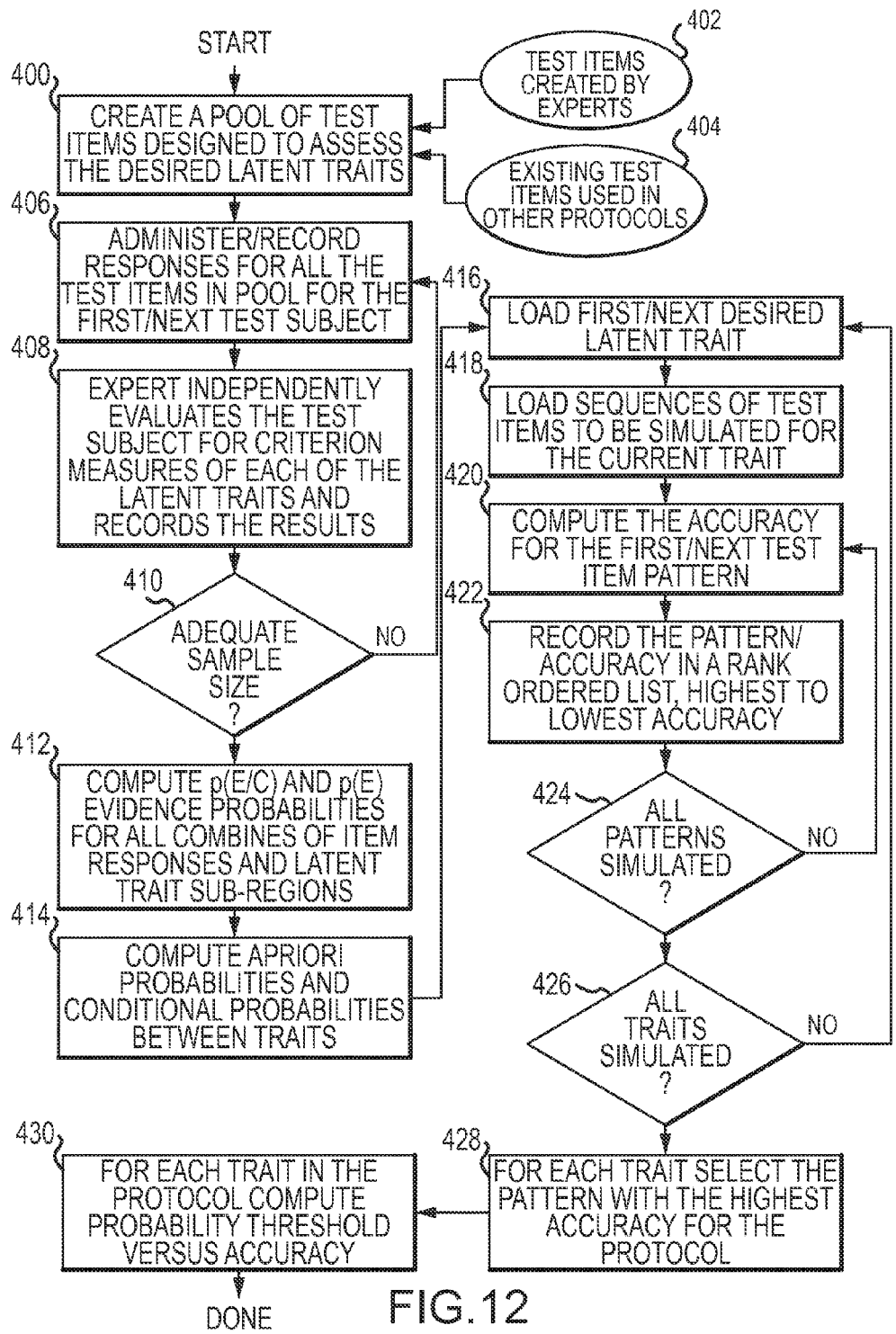
FIG. 12 illustrates a flowchart of an exemplary method for designing and validating new protocols of test items.

In this regard, FIG. 12 illustrates a flow chart of an exemplary method for designing and validating protocols of test items, e.g., selecting and ordering test items to be administered to a test subject. In step 400 a pool of test items is created, designed to assess the desired latent trait(s) in the new protocol. The test items can be existing test items used in other protocols 404 such as the PHQ-9 or test items created by domain experts 402 (e.g., trained professionals such as psychologists or psychiatrists, preferably with training in psychometrics). In step 406 all of the test items in the pool are administered to a test subject and the responses are recorded. In step 408 an expert independently evaluates the test subject for criterion measures of each of the latent traits in the pool. If step 408 is performed at the time of (e.g., concurrently with) step 406 then the test items provide concurrent evidence. If step 408 is performed at a later time, the test items provide predictive evidence. Steps 406 and 408 are repeated for subsequent test subjects until an adequate sample size is reached to form a validated evidence data set. Steps 400 through 410 comprise the design and data collection phases of a validation study and the recorded response and criterion measures comprise the validated evidence data set.

In step 412 the conditional response probability of a specific response when the test subject is located in a specific sub-region $p(E|C)$ and the overall response probability of a specific response $p(E)$ are determined for all combinations of item responses and latent trait sub-regions. These are the validated evidence probability data sets that may be used in the probabilistic scoring outlined above (e.g., data sets 108, 212, and 312).

In step 414, using the criterion measure results from step 412, the apriori probabilities of all trait sub-regions are determined and used as a potential validated evidence probability data set for prior sub-region probabilities used in the probabilistic scoring outlined above (e.g., data sets 102, 202 and 302). In addition, using the criterion measure results, the conditional probabilities between traits are computed and used as a potential data source for prior sub-region probabilities based on prior results used in the probabilistic scoring outlined above (e.g., at step 324 in FIG. 11).

Once the evidence has been compiled and a set of apriori and conditional probabilities between latent traits have been generated at step 414, simulations can be run using the validated evidence probabilities to perform the probabilistic scoring from the validated evidence data set as input data. The simulation process starts in step 416 by loading the first latent trait. In step 418 the patterns of test items to be explored are loaded for the latent trait loaded in step 416. The patterns of test items may consist of any combination and/or ordering of test items in the original test item pool.

In step 420, accuracy of the test item sequence in step 418 is determined using probabilistic scoring to determine a result for the input data cases from the validated evidence data set and comparing the result to the associated criterion measure. Sensitivity of each latent trait sub-region (the percentage of times the computed sub-region is the result when the criterion sub-region is also the result) and specificity of each latent trait sub-region (the percentage of times the computed sub-region is not the result when the criterion sub-region is also not the result) may be used as the measure of accuracy. In step 422 the pattern and its determined accuracy may be placed on a rank ordered list, highest to lowest accuracy, based first on specificity and then on sensitivity.

At step 424, the sequences in step 418 are checked to see if all the possible sequences have been simulated. If not, execution may go back to step 420 to simulate the next sequences. In step 426, the set of traits in the original pool are checked to see if all the latent traits have been simulated. If not, execution may go back to step 416 to load the next trait. When all the patterns for all the traits have been simulated, step 428 may go through the rank ordered list of accuracies and for each trait selects the sequence with the highest accuracy for the new protocol. At step 430, the probability threshold versus accuracy curves may be determined (e.g., FIG. 10) for each trait in the new protocol.

The collection of validated evidence data sets, the computed $p(E|C)$ and $p(E)$ evidence probabilities, the computed apriori probabilities, the computed conditional probabilities between traits and the protocols with their validated accuracies and probability thresholds, comprise a knowledge base for psychometric measures. Combined with the simulator functionality (FIG. 12), new protocols of test items may be easily generated and validated to meet the needs of specific applications.

As is noted above, the foregoing systems and methods may be implemented using electronic devices for executing one or more of the method steps. For example, an electronic instrument may be self-contained, whereby the instrument may include a database (e.g., a computer readable storage medium) containing validated evidence data sets (e.g., validated evidence probability data sets) that is operatively coupled to one or more processors for executing the determination of sub-region probabilities and/or differential probabilities. Such a device may also include a graphical user interface (GUI) for presenting test items to a test subject and means for receiving and/or recording responses from the test subject, such as input keys or a touch screen, for example.

According to one exemplary embodiment, and referring to FIG. 13, a method and system for assessing latent trait(s) using probabilistic scoring may be implemented over a computer network system such as computer network system 500. The network system 500 may include a host server system 508 which executes the method steps such as the determination of sub-region probabilities and/or severity for a test subject. The host server system 508 may include a host server 510 including one or more processors (e.g., computer microprocessors) that are coupled to a data storage device 512 (e.g., a computer-readable storage medium comprising disk drives and/or solid state drives) for the retrieval and storage of data. The data storage device 512 may include, for example, a computer-readable storage medium having one or more sets of instructions embodied thereon for carrying out the method steps described herein.

The method may be executed entirely by the host server system 508, although it will be appreciated that some or all of the tasks required to carry out the methods may be carried out by a third party system that is coupled to the host server system 508, e.g., over network 502.

It will also be appreciated that more than one server may be utilized by the host server system 508. Further, communications between the host server 510 and the data storage device 512 may be implemented by any suitable networking infrastructure known in the art including hard-wired communication, wireless technology, radio-based communications, telephony-based communications or a combination of the above.

The host server system 508 may communicate with client devices 504a-c through a network 502. Network 502 may be any type of network including but not limited to the internet, a local area network (LAN), a wide area network (WAN), a telephone network or any other communication network or combination of networks that facilitates access and transfer of data among remote locations. Client devices 504a-c may be any digital device, including, but not limited to a desktop computer, a laptop computer, a mobile telephone device, a PDA, a smart phone, a tablet or the like. Client devices 504a-c may include, for example, internet browser applications 506a-c (e.g., Microsoft Internet Explorer or the like) for providing a communication interface with the network 502 and for displaying GUIs generated by the host server system 508. Responses from a test subject using a client device may be transmitted to the server system 508 sequentially (e.g., as soon as the test subject responds to a test item) to provide dynamic administration of the test items and provide the ability to terminate the administration of test items over the client device once a threshold probability is reached. Alternatively, the client device may store the responses for later uploading to the host server system 508.

EXAMPLE

A measurement instrument to assess depression in a test subject is provided. The test subject is identified as a Caucasian female presenting at a rural Federally Qualified Health Center (FQHC). It is known from a validated evidence data sets that a Caucasian female at this type of practice has a 54.4% probability of lying within the sub-region No Depression, a 14.3% probability of lying within the sub-region Sub-Threshold Depression and a 31.3% probability of lying within the sub-region Major Depression. These probabilities are used as prior probabilities.

An initial test item is administered to the test subject that elicits the test subject to respond with answers coded 1, 2, 3, or 4 to the test item. The test subject responds with a 1 to the test item. It is known from validated evidence data sets that the probability of a test subject answering 1 to the initial test item is 47.1%. Further, it is also known from validated evidence data sets that the conditional response probabilities of answering 1 to this test item when a test subject lies in a given sub-region is as listed in Table 1.

TABLE 1

| Sub-Region | Conditional Probability of Answering 1 |
|---|---|
| No depression | 72.3% |
| Sub-Threshold depression | 23.5% |
| Major depression | 14.2% |

Based on the test subject's response to the initial test item, the sub-region probability for No Depression is determined to be:

$$P(C \mid E) = \frac{(0.723) \cdot (0.544)}{0.471} = 0.835$$

Similarly, the sub-region probability for Sub-Threshold Depression is determined to be:

$$P(C \mid E) = \frac{(0.235) \cdot (0.143)}{0.471} = 0.071$$

Finally, the sub-region probability for Major Depression is determined to be:

$$P(C \mid E) = \frac{(0.142) \cdot (0.313)}{0.471} = 0.094$$

These sub-region probability values are normalized to 1, and the results are listed in Table 2.

TABLE 2

| Sub-Region | Sub-Region Probability |
|---|---|
| No depression | 83.5% |
| Sub-Threshold depression | 7.1% |
| Major depression | 9.4% |

These sub-region probabilities for the test subject may then be used as prior probabilities in a subsequent sub-region probability determination. In this regard, a subsequent test item is administered to the test subject that again elicits the test subject to respond 1, 2, 3, or 4 to the subsequent test item. The test subject responds with a 2 to the test item. It is known from validated evidence probability data sets that the probability of a test subject answering 2 to the second test item is 28.7%. Further, it is also known from validated evidence probability data sets that the conditional response probabilities of answering 2 to this subsequent test item when a test subject lies in a given sub-region is as listed in Table 3.

TABLE 3

| Sub-Region | Conditional Probability of Answering 2 |
|---|---|
| No depression | 20.1% |
| Sub-Threshold depression | 66.9% |
| Major depression | 26.1% |

Based on the test subject's response to this subsequent test item, the sub-region probability for No Depression is refined to be:

$$P(C \mid E) = \frac{(0.201) \cdot (0.835)}{0.287} = .585$$

Further, the test subject's refined sub-region probability for Sub-Threshold Depression is determined to be:

$$P(C \mid E) = \frac{(0.669) \cdot (0.071)}{0.287} = .165$$

Finally, the sub-region probability for Major Depression is determined to be:

$$P(C \mid E) = \frac{(0.261) \cdot (0.094)}{0.287} = .085$$

These sub-region probability values are normalized to 1, and the results are listed in Table 4.

TABLE 4

| Sub-Region | Sub-Region Probability |
|---|---|
| No depression | 70.0% |
| Sub-Threshold depression | 19.7% |
| Major depression | 10.3% |

If this process is continued for a response case where the test subject answers 2 for all the remaining five questions, the results might look like those listed in Table 5.

TABLE 5

| Sub-Region | Sub-Region Probabilities After Each Answer | | | | | | |
|---|---|---|---|---|---|---|---|
| No depression | 83.5% | 70.0% | 64.1% | 57.2% | 36.3% | 11.4% | 2.9% |
| Sub-Threshold depression | 7.1% | 19.7% | 31.7% | 41.3% | 62.9% | 88.1% | 96.8% |
| Major depression | 9.4% | 10.3% | 4.2% | 1.5% | 0.8% | 0.5% | 0.3% |

If a threshold probability of 90% were being used the test item sequence could be terminated after the seventh question when probability of the Sub-Threshold Depression rises to 96.8%. The computed result is Sub-Threshold Depression.

Applying logic to determine which differential probability value to use for the severity, since the No Depression probability is greater than the Major Depression probability the Sub-Threshold Depression minus No Depression differential probability value (shifted by one) should be used. The severity score is then 1.94 (0.968−0.029+1) on a scale of 0 to 4.

While various embodiments of the present invention have been described in detail, it is apparent that modifications and adaptations of those embodiments will occur to those skilled in the art. However, is to be expressly understood that such modifications and adaptations are within the spirit and scope of the present invention.

What is claimed is:

1. A method for assessing a latent trait in a test subject, comprising the steps of:
   providing a graphical user interface for allowing the input of a test subject's first test item responses to a plurality of first test items that are administered to the test subject to elicit the first test item responses from the test subject;
   receiving the test subject's responses to at least an initial first test item and a subsequent first test item;
   determining, using one or more processors, an initial first sub-region probability of the test subject lying within a first sub-region of a first latent trait from the test subject's response to the initial first test item; and
   determining, using one or more processors, a subsequent first sub-region probability of the test subject lying within the first sub-region of the first latent trait using:
   the test subject's response to the subsequent first test item to ascertain a conditional response probability, and
   the initial first sub-region probability as a prior first sub-region probability.

2. The method recited in claim 1, wherein the conditional response probability is ascertained from one or more validated evidence data sets.

3. The method recited in claim 1, further comprising the step of determining, using the processor, a further first sub-region probability of the test subject lying within the first sub-region of the first latent trait using:
   the test subject's response to a further first test item to ascertain a further conditional response probability; and
   the subsequent first sub-region probability as a prior sub-region probability.

4. The method recited claim 1, further comprising the steps of determining, using a processor, an initial second sub-region probability of the test subject lying in a second sub-region of the first latent trait from the test subject's first test item response to the initial first test item and determining a subsequent second sub-region probability of the test subject lying within the second sub-region of the first latent trait.

5. The method recited in claim 4, further comprising the step of determining, using the processor, a differential probability value between the probability of the first and second sub-regions of the first latent trait after determining the subsequent sub-region probability of the test subject lying within the second sub-region and determining a subsequent sub-region probability of the test subject lying within the first sub-region.

6. The method recited in claim 5, further comprising the step of administering the plurality of first test items to the test subject through the graphical user interface.

7. The method recited in claim 6, wherein the first test items are administered to the test subject sequentially.

8. The method recited in claim 7, further comprising the step of terminating the administering of the first test items to the test subject when the differential probability value reaches a terminus differential probability value that meets or exceeds a threshold differential probability value.

9. The method recited in claim 5, further comprising the step of determining a severity score for the first latent trait in the test subject from the differential probability value.

10. The method recited in claim 9, wherein the severity score for the first latent trait is determined by mapping the differential probability value to a severity score validated evidence data set.

11. The method recited in claim 1, wherein the first latent trait is a psychiatric disorder.

12. The method recited in claim 11, wherein the first latent trait is selected from the group consisting of depression, dysthymic disorder, bipolar disorder, generalized anxiety disorder, obsessive-compulsive disorder, post-traumatic stress disorder, a psychotic disorder, a personality disorder, a sleeping disorder, an eating disorder, a developmental disorder or a substance dependency.

13. The method recited in claim 11, wherein the first latent trait is depression.

14. The method recited in claim 1, wherein the subsequent sub-region probabilities of all first latent trait sub-regions are determined and are normalized to one.

15. The method recited in claim 1, wherein the plurality of first test items comprise agreement test items that elicit the test subject to indicate a level of agreement or disagreement with a concept.

16. The method recited in claim 15, wherein the agreement test items elicit a level of agreement on a Liked scale.

17. The method recited in claim 1, wherein the test items comprise physiological test items that elicit the test subject to indicate the presence or absence of a physiological condition.

18. The method recited in claim 1, wherein the initial first sub-region probability is determined using an apriori probability of the test subject lying in the first sub-region of the first latent trait.

19. The method recited in claim 1, wherein the initial and subsequent first sub-region probabilities are determined using Bayesian inferences.

20. The method recited in claim 1, wherein the step of administering the plurality of first test items to the test subject comprises administering at least three first test items to the test subject.

21. The method recited in claim 1, wherein the step of administering the plurality of first test items to the test subject comprises administering at least four first test items to the test subject.

22. The method recited in claim 1, further comprising steps of:
receiving the test subject's responses to a plurality of second test items that are administered to the test subject to elicit second test item responses from the test subject;
determining an initial first sub-region probability of the test subject lying within a first sub-region of a second latent trait from:
i) the test subject's response to an initial test item from the plurality of second test items to ascertain a conditional sub-region probability for the second latent trait, and
ii) the subsequent first sub-region probability of the test subject lying within the first sub-region of the first latent trait as a prior second sub-region probability for the second latent trait.

23. The method recited in claim 22, wherein the second latent trait is a psychiatric disorder.

24. The method recited in claim 23, wherein the first latent trait is depression and the second latent trait is generalized anxiety disorder.

25. The method recited in claim 1, wherein the initial first sub-region probability of the test subject lying within the first sub-region of the first latent trait is determined before receiving the subsequent first test item from the test subject.

26. A method for assessing a latent trait in a test subject, comprising the steps of:

(a) administering, through a graphical user interface, a test item from a plurality of first test items to a test subject to elicit a response to the first test item from the test subject;
(b) determining, using one or more processors, sub-region probabilities of the test subject lying within each of a plurality of sub-regions of a first latent trait from the test subject's response to the first test item;
(c) determining, using the one or more processor, a differential probability value between at least first and second adjacent sub-regions of the first latent trait; and
(d) repeating steps (a) to (c) until the differential probability value between the first and second sub-regions is a terminus differential probability value that meets or exceeds a threshold differential probability value.

27. The method recited in claim 26, further comprising the step of:
determining a severity score for the first latent trait in the test subject from the terminus differential probability value.

28. The method recited in claim 27, wherein the severity score for the first latent trait is determined by mapping the terminus differential probability value to a severity score validated evidence data set.

29. The method recited in claim 26, wherein the step of determining the sub-region probabilities of the test subject lying within each of the plurality of sub-regions of the first latent trait comprises determining the sub-region probabilities using:
i) the test subject's response to the test item to determine a conditional sub-region probability; and
ii) a previously determined sub-region probability of the test subject lying within each of the plurality of sub-regions of the first latent trait as a prior sub-region probability.

30. The method recited in claim 26, wherein the sub-region probabilities are determined using Bayesian inferences.

31. The method recited in claim 26, wherein the first latent trait is a psychiatric disorder.

32. The method recited in claim 26, wherein the first latent trait is selected from the group consisting of depression, dysthymic disorder, bipolar disorder, generalized anxiety disorder, obsessive-compulsive disorder, post-traumatic stress disorder, a psychotic disorder, a personality disorder, a sleeping disorder, an eating disorder, a developmental disorder or a substance dependency.

33. The method recited in claim 26, wherein the first latent trait is depression.

34. The method recited in claim 26, wherein the sub-region probabilities of the test subject lying within each of the plurality of sub-regions of the first latent trait are normalized to one before determining a differential probability value.

35. The method recited in claim 26, wherein the plurality of first test items comprise agreement test items that elicit the test subject to indicate a level of agreement or disagreement with a concept.

36. The method recited in claim 35, wherein the agreement test items elicit a level of agreement on a Liked scale.

37. The method recited in claim 26, wherein the plurality of first test items comprise physiological test items that elicit the test subject to indicate the presence or absence of a physiological condition.

* * * * *